US00PP29397P2

(12) United States Plant Patent
Egger

(10) Patent No.: US PP29,397 P2
(45) Date of Patent: Jun. 12, 2018

(54) ***HEUCHERA* PLANT NAMED 'TNHEUNEA'**

(50) Latin Name: ***Heuchera* hybrid**
Varietal Denomination: TNHEUNEA

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 43 days.

(21) Appl. No.: 15/530,250

(22) Filed: Dec. 13, 2016

(51) Int. Cl.
*A01H 5/12* (2018.01)
*A01H 5/02* (2018.01)

(52) U.S. Cl.
USPC ..... Plt./440
CPC ..... *A01H 5/02* (2013.01); *A01H 5/12* (2013.01)

(58) Field of Classification Search
USPC ..... Plt./440
See application file for complete search history.

*Primary Examiner* — Anne Marie Grunberg
(74) *Attorney, Agent, or Firm* — Klarquist Sparkman, LLP

(57) ABSTRACT

A new and distinct *Heuchera* plant characterized by amber colored leaves, medium size, slightly lobed, geranium-like leaves, yellow green flowers in short spikes in spring, not free flowering, good sun tolerance, a medium large, mounding habit with excellent crown count, and excellent vigor.

1 Drawing Sheet

Botanical denomination: *Heuchera* hybrid.
Variety designation: 'TNHEUNEA'.

BACKGROUND OF THE INVENTION

The present invention relates to a new and distinct cultivar of *Heuchera* and given the cultivar name of 'TNHEUNEA'. *Heuchera* is in the family Saxifragaceae. *Heuchera* 'TNHEUNEA' originated as a controlled cross using *Heuchera* 'K993-5', a proprietary, unpatented, unnamed plant as the seed parent, and *Heuchera* 'K1000-1', a proprietary, unpatented, unnamed plant as the pollen parent. These parents are a result of breeding using hardy *Heuchera richardsonii* with proprietary hybrid lines. *Heuchera* 'TNHEUNEA' was bred to be a large, hardy, landscape plant with leaves of a solid color.

Compared to the seed parent, *Heuchera* 'K993-5', the new cultivar has amber leaves rather than lime.

Compared to the pollen parent, *Heuchera* 'K1000-1', the new cultivar has a larger habit.

Compared to *Heuchera* 'Cherry Cola', U.S. Plant Pat. No. 22,967, the new cultivar has a larger habit and larger leaves. The foliage of the new cultivar is amber colored rather than soft red. The flowers of the new cultivar are yellow green rather than rust red.

This new *Heuchera* is uniquely distinguished by:

1. amber colored leaves,
2. medium size, slightly lobed, geranium-like leaves,
3. yellow green flowers in short spikes in spring, not free flowering
4. good sun tolerance,
5. a medium large, mounding habit with excellent crown count, and
6. excellent vigor.

This new cultivar has been reproduced only by asexual propagation (tip cuttings and tissue culture using growing tips). Each of the progeny exhibits identical characteristics to the original plant. Asexual propagation in 2013 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows 18-month-old plants of *Heuchera* 'TNHEUNEA' just beginning to flower growing in the trial bed in late April in Canby, Oreg.

FIG. 2 shows three-year-old plants in mid-July in the trial beds in Canby, Oreg.

DETAILED PLANT DESCRIPTION

The following is a detailed description of the new *Heuchera* cultivar based on observations taken in April of one-year-old specimens growing in the trial field in June in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The *Royal Horticultural Society Colour Chart*, 5$^{th}$ edition, 2007.

Plant:

*Form.*—Basal rosette, herbaceous perennial.

*Hardiness.*—USDA Zone 4 to 9.

*Size.*—20 cm tall from top of the foliage to the ground and 38 cm wide.

*Number of crowns.*—About 20.

*Habit*.—Medium, mounding.
*Vigor*.—Excellent.

Leaf:
*Type*.—Simple.
*Arrangement*.—Rosette.
*Shape*.—Broadly ovate to orbicular.
*Number*.—About 200.
*Blade size*.—Grows to 11 cm long and 9.5 cm wide.
*Venation*.—Palmate.
*Lobing/division*.—7 shallow palmate lobes.
*Margins*.—Crenate, slightly undulate.
*Apex*.—Mucronulate.
*Base*.—Cordate, strongly overlapping and sometimes spiraling in.
*Surface texture*.—Glandular-puberulent on both sides.
*Leaf rugosity*.—Absent.
*Petiole description*.—Grows to 15 cm long and 3.5 mm wide, glandular hairs, Greyed Orange 177B.
*Leaf color*.—Variable depending on temperature and light: spring new leaves, top side Greyed Orange 175B, veins 174D, bottom side Greyed Purple 183D with veins 177D; mature leaves late spring leaves topside Greyed Orange 165C, veins 165B, bottom side Greyed Purple 182B, veins 165B; summer leaves Greyed Orange 164A to 164C, sometimes tinted Greyed Red 178B.

Inflorescence:
*Size*.—Grows to 7 cm wide and 12 cm long.
*Type*.—Upright thyrse.
*Number of flowers per thyrse*.—About 210.
*Number of thyrse*.—About 4.
*Peduncle*.—Grows to 36 cm long and 3 mm wide at base, glandular hairs, Greyed Purple 183B.
*Pedicel*.—Grows to 2 mm long, with glandular hairs, Greyed Purple 183B.
*Bloom period*.—Late April to June in Canby, Oreg.

Flower bud:
*Size*.—2 mm wide and 3 mm long.
*Description*.—Glandular puberulent, ovoid, down facing.
*Color*.—Yellow Green 152D.

Flower:
*Type*.—Perfect.
*Shape*.—Campanulate.
*Attitude*.—Side and down-facing.
*Size*.—5 mm long and 3 mm wide.
*Corolla description*.—5 petals, each 2.5 mm long and less than 1 mm wide, spatulate, margins entire, tip acute, glandular-puberulent on backside, glabrous inside, both sides Yellow Green 152D.
*Calyx description*.—Campanulate, 4 mm long and 3 mm wide, with 5 lobes with wide sinuses divided ½ way to the base, each 1.5 mm wide and 2 mm long, oblong in shape, back side glandular-puberulent with glandular hairs (Greyed Purple 183B), glabrous inside, tip obtuse, margin entire, both sides Yellow Green 152D.
*Stamen description*.—5 in number, filaments 1 mm long, Yellow Green 152D, anthers 0.5 mm long, Orange 26A, pollen none.
*Pistil description*.—1, 2-beaked, 5 mm long and 2 mm wide, Yellow Green 152D overall, ovary 2 mm long and 2 mm wide, style 2 mm long.
*Fragrance*.—None.
*Lastingness*.—Each thyrse blooms for about 3 weeks on the plant.

Fruit and seed: None seen.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

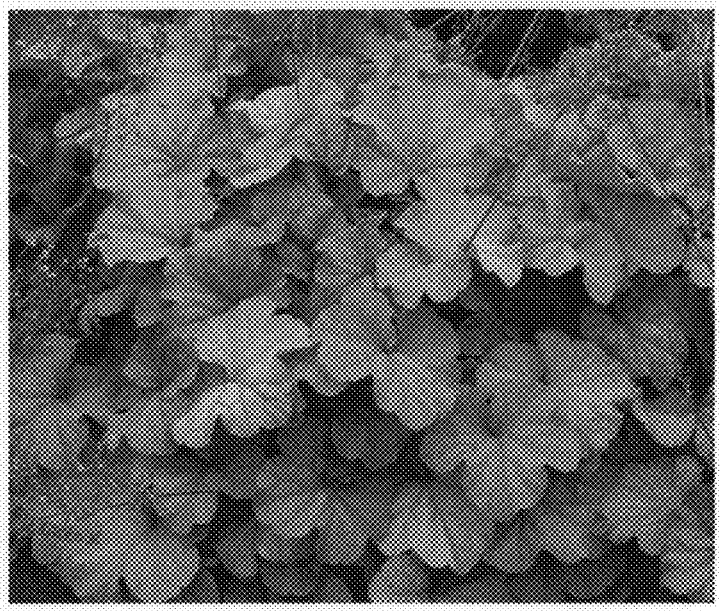

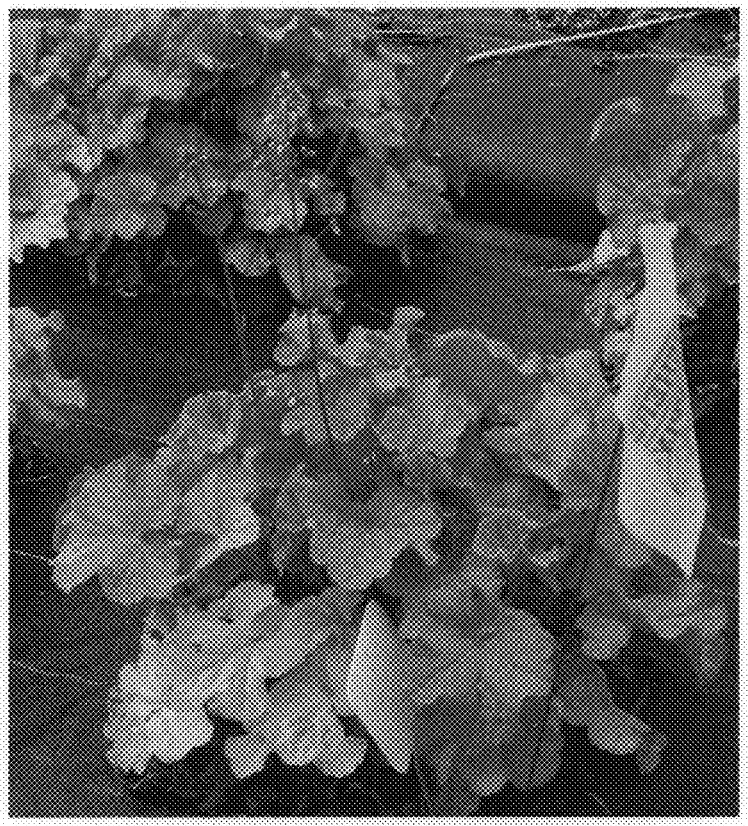
FIG. 1 above
FIG. 2 below